United States Patent

Pi et al.

[11] Patent Number: 5,589,450
[45] Date of Patent: Dec. 31, 1996

[54] PROCESS FOR THE PRODUCTION OF WATER-FREE DETERGENT MIXTURES

[75] Inventors: Raphael Pi, Granollers; Joaquim Bigorra-Losas, Sabadell; Oriol Ponsati-Obiols, Barcelona, all of Spain; Karl Schmid, Mettmann, Germany

[73] Assignee: Henkel Kommanditgesellschaft auf Aktien, Duesseldorf, Germany

[21] Appl. No.: 505,305

[22] PCT Filed: Feb. 11, 1994

[86] PCT No.: PCT/EP94/00392

§ 371 Date: Sep. 15, 1995

§ 102(e) Date: Sep. 15, 1995

[87] PCT Pub. No.: WO94/19313

PCT Pub. Date: Sep. 1, 1994

[30] Foreign Application Priority Data

Feb. 19, 1993 [DE] Germany ............ 43 05 083.2

[51] Int. Cl.$^6$ .............. C11D 3/28; C11D 3/30; C11D 1/72

[52] U.S. Cl. ............ 510/535; 510/413; 510/423; 510/499

[58] Field of Search ............ 252/546, 174.21, 252/544, 542; 562/553, 554, 561; 564/296; 554/68

[56] References Cited

U.S. PATENT DOCUMENTS

| | | | |
|---|---|---|---|
| 4,830,783 | 5/1989 | Broze et al. | 252/545 |
| 5,281,749 | 1/1994 | Uphues et al. | 562/40 |

FOREIGN PATENT DOCUMENTS

| | | |
|---|---|---|
| 0243619 | 11/1987 | European Pat. Off. . |
| 0302329 | 2/1989 | European Pat. Off. . |
| 0353580 | 2/1990 | European Pat. Off. . |
| 2063424 | 7/1972 | Germany . |
| 2926479 | 11/1980 | Germany . |
| 3939264 | 11/1989 | Germany . |
| 4040887 | 7/1992 | Germany . |
| 4207386 | 8/1993 | Germany . |
| 2022125 | 12/1979 | United Kingdom . |

OTHER PUBLICATIONS

Parf. Cosm. Arom. 70, 67 (1986).
Soap Cosm. Chem. Spec. 46 (Apr. 1990).

*Primary Examiner*—Erin M. Harriman
*Attorney, Agent, or Firm*—Wayne C. Jaeschki; John E. Drach; Henry E. Millson, Jr.

[57] ABSTRACT

Water-free detergent mixtures may be obtained by reacting secondary or tertiary amines with alkylating agents, in a per se known manner, in the presence of fatty alcohol polyglycol ethers with a HLB value in a range from 6 to 12, but without adding water or organic solvents. These products are suitable for preparing surface-active agents.

16 Claims, No Drawings

PROCESS FOR THE PRODUCTION OF WATER-FREE DETERGENT MIXTURES

BACKGROUND OF THE INVENTION

1. Field of the Invention

This invention relates to a process for the production of water-free detergent mixtures, in which amines are alkylated in the presence of nonionic surfactants, to the products obtained by this process and to their use in surface-active compositions.

2. Statement of Related Art

Amphoteric or zwitterionic surfactants are highly compatible with the skin and show excellent cleaning properties. Accordingly, they are particularly suitable for use in the production of a number of surface-active products. In the most simple case, they are produced by reaction of secondary or tertiary amines with sodium chloroacetate to form alkyl betaines. The reaction of fatty acid amidoamines or imidazolines with sodium chloroacetate leads to the formation of amphoteric surfactants of the glycinate type. If an acrylate is used as the alkylating agent, aminopropionates are formed. Compounds of the type mentioned are described in a number of synoptic articles among which only Parf. Cosm. Atom. 70, 67 (1986), HAPPI, 70 (November 1986) and Soap Cosm. Chem. Spec. 46 (April 1990) are cited here.

A particular concern in the production of amphoteric or zwitterionic surfactants is to produce highly concentrated but free-flowing products in order thus to minimize transport and storage costs. In addition, the basically excellent compatibility of the products with the skin must not be impaired by traces of unreacted alkylating agent and phase separation through an excessive electrolyte content must be avoided.

There has been no shortage of attempts in the past to solve one or more of the problems mentioned. Thus, DE-A 29 26 479 (Goldschmidt) describes a process for the production of alkyl amidobetaines in which the residual content of alkylating agent is minimized by carrying out the reaction at a pH value of 7.5 to 10.5. The teaching of DE-A 20 63 424 (Rewo), which describes pH regulation for the alkylation of imidazolines, points in the same direction.

According to DE-A1 40 40 887 (Goldschmidt), the quaternization reaction involved in the production of free-flowing, aqueous betaine dispersions is carried out in aqueous or alcoholic solution with addition of anionic surfactants. In addition, it is known from GB-A 20 22 125 that $C_{12/14}$ cocoalkyl dimethylamine can be alkylated with sodium chloroacetate in the presence of an aqueous solution of sodium lauryl sulfate. However, it is expressly pointed out in both documents that the presence of water during the alkylation reaction is absolutely essential because otherwise non-flowable products with a lamellar liquid crystal structure would be formed. Accordingly, the processes mentioned give highly concentrated, but not water-free surfactant pastes.

Another process for the production of flowable and pumpable betaines with an active substance content of at least 70% by weight is known from EP-B10 243 619 (Goldschmidt). According to this document, amidoamines with a melting point of at most 30° C. are used as the sole starting materials and the quaternization reaction is carried out with potassium or ammonium chloroacetate in an organic solvent which may contain at most 20% by weight of water. However, a process such as this is hardly suitable for operation on an industrial scale because the necessary separation of the solvent from the useful product on completion of the alkylation reaction would involve considerable outlay on equipment.

In addition, it is known from EP-B1 0 302 329 (Goldschmidt) that free-flowing betaine pastes with a content of around 40% by weight can be produced by concentrating the aqueous betaine solutions obtained by conventional quaternization processes to the desired water content by evaporation and subsequently adjusting the pH to a value of 1 to 4.5 by addition of mineral acid.

According to EP-A2 0 353 580 (Goldschmidt), concentrated, free-flowing, aqueous solutions of betaines optionally containing lower aliphatic alcohols are produced by carrying out the quaternization in aqueous or aqueous-alcoholic solution with addition of nonionic surfactants in such a quantity that the resulting solution has a nonionic surfactant content of, preferably, 3 to 20% by weight. Suitable nonionic surfactants are, above all, fatty acid polyethylene oxide esters. Fatty alcohol alkoxylates with an HLB value of 14 to 20 are mentioned as other suitable, but specifically not preferred surfactants. However, this document teaches carrying out the quaternization in the presence of water and/or alcohols, preferably ethanol, and adding extremely hydrophilic, nonionic surfactants, for example polysorbates containing 120 ethylene oxide units, to the betaines before, but preferably after, the quaternization to reduce their viscosity. Accordingly, water-free products cannot be produced by this process either. Another disadvantage is that compounds of betaines and extremely hydrophilic nonionic surfactants are unavoidably obtained, the nonionic surfactants in question being unsuitable for cosmetic products or dishwashing detergents on account of their inadequate foaming.

Accordingly, the problem addressed by the present invention was to provide amphoteric surfactants in water-free form and, at the same time, to avoid the disadvantages of the prior art.

DESCRIPTION OF THE INVENTION

The present invention relates to a process for the production of water-free detergent mixtures, in which secondary or tertiary amines are reacted with alkylating agents in known manner in the presence of fatty alcohol polyglycol ethers with an HLB value of 6 to 12, but without any addition of water or other solvents.

It has surprisingly been found that comparatively hydrophobic fatty alcohol polyglycol ethers with an HLB value of 6 to 12 are particularly suitable as solvents for the quaternization of secondary or tertiary amines, so that the use of water, alcohols or other organic solvents at this stage is avoided. At the same time, completely water-free detergent mixtures with a high content of amphoteric or zwitterionic surfactants are accessible for the first time by the process according to the invention. The invention also includes the discovery, which was not obvious in the light of EP-A2 0 353 580, that the betaine compounds resulting from the alkylation form mixed micelles, but not high-viscosity, liquid crystalline phases with the comparatively hydrophobic nonionic surfactants selected virtually irrespective of the mole fraction. Accordingly, the water-free detergent mixtures are surprisingly low in viscosity and stable, i.e. neither phase separation nor the precipitation of inorganic salts is observed.

Amines

The amine components may be secondary and, in particular, tertiary amines. Suitable starting materials are, for example, dialkyl and preferably trialkylamines corresponding to formula (I):

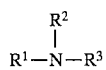

in which $R^1$ represents alkyl and/or alkenyl radicals containing 6 to 22 carbon atoms, $R^2$ represents hydrogen or alkyl radicals containing 1 to 4 carbon atoms and $R^3$ represents alkyl radicals containing 1 to 4 carbon atoms.

Typical examples are hexyl methylamine, hexyl dimethylamine, octyl dimethylamine, decyl dimethylamine, dodecyl methylamine, dodecyl dimethylamine, dodecyl ethyl methylamine, $C_{12/14}$ cocoalkyl dimethylamine, myristyl dimethylamine, cetyl dimethylamine, stearyl dimethylamine, stearyl ethyl methylamine, oleyl dimethylamine, $C_{16/18}$ tallow alkyl dimethylamine and technical mixtures thereof.

Other suitable starting materials are amidoamines corresponding to formula (II):

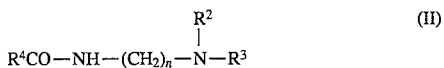

in which $R^4CO$ is an aliphatic acyl radical containing 6 to 22 carbon atoms and 0 or 1 to 3 double bonds, n is 0 or a number of 1 to 3 and $R^2$ and $R^3$ are as defined above.

Amidoamines are known compounds which may be obtained by the relevant methods of preparative chemistry. One process for their production comprises, for example, amidating fatty acids with diamines. Typical examples are reaction products of $C_{6-22}$ fatty acids, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethyl aminoethylamine, N,N-dimethyl aminopropylamine, N,N-diethyl aminoethylamine and N,N-diethyl aminopropylamine. $C_{12/14}$ cocofatty acid N,N-dimethyl aminopropylamide is preferably used.

Other suitable amines are imidazolines corresponding to formula (III):

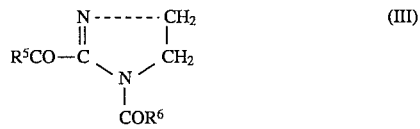

in which $R^5CO$ and $R^6CO$ independently of one another represent aliphatic acyl radicals containing 6 to 22 carbon atoms and 0 or 1 to 3 double bonds.

These substances are also known compounds which may be obtained, for example, by cyclizing condensation of 2 moles of fatty acid with ethylenediamine.

Typical examples are condensation products of the above-mentioned fatty acids with ethylenediamine, preferably imidazolines based on lauric acid or, again, $C_{12/14}$ cocofatty acid.

Fatty alcohol polyglycol ethers

The fatty alcohol polyglycol ethers to be used in the process according to the invention are comparatively hydrophobic compounds with an HLB value of 6 to 12 and preferably 8 to 11.

The fatty alcohol polyglycol ethers correspond to formula (IV):

in which $R^7$ is an alkyl radical containing 8 to 14 carbon atoms, $R^8$ is hydrogen or a methyl group and n is a number of 1 to 10.

Typical examples are addition products of, on average, 1 to 10 moles of ethylene oxide and/or propylene oxide with caprylic alcohol, capric alcohol, lauryl alcohol, myristyl alcohol or, in particular, $C_{12/14}$ cocofatty alcohol. Adducts of, on average, 0 to 2 moles of propylene oxide and 3 to 8 moles of ethylene oxide with octanol or $C_{12/14}$ cocofatty alcohol are preferably used. The adducts may have a conventional, broad homolog distribution and, hence, a residual content of free fatty alcohol. However, one preferred embodiment of the invention is characterized by the use of fatty alcohol polyglycol ethers with a narrow homolog distribution, so-called narrow-range ethoxylates (NRE), which are substantially free from fatty alcohol and provide for a particularly low final viscosity in the detergent mixtures according to the invention.

The amines and the fatty alcohol polyglycol ethers may be used in a molar ratio of 2:1 to 1:2. However, a molar ratio of 1.8:1 to 1:1.2 has proved to optimal so far as the performance properties of the resulting detergent mixtures are concerned.

Alkylating agents

Halocarboxylic acids and alkali metal salts or esters thereof may be used as alkylating agents. Sodium chloroacetate is preferably used by virtue of its ready availability. The amines and the halocarboxylic acids or their salts may be used in a molar ratio of 1:1.0 to 1:1.2 and preferably in a molar ratio of 1:1 to 1:1.15.

Quaternization

The quaternization or betainization of the amines may be carried out in known manner. In contrast to known processes, the presence of a further solvent, especially water, is definitely not necessary nor desirable because otherwise water-free products would not be obtained. The alkylation reaction is typically carried out at temperatures of 70° to 98° C. and is complete in 1 to 10 hours and preferably 3 to 7 hours.

To ensure that the alkylating agent is completely reacted off, it has proved to be of advantage to carry out the reaction at a pH value of 6 to 10 and preferably at a pH value of 7 to 8.5. Another method of minimizing the residual content of alkylating agent is to add a defined excess of amino acids, particularly glycine to the reaction mixture on completion of the alkylation, as described in DE-A1 39 39 264 (Henkel).

The present invention includes the further observation that the absence of water during the alkylation reduces the alkylation of the polyglycol ether taking place as a competitive reaction to a minimum. Accordingly, the content of ether carboxylic acids in the products obtainable by the process according to the invention is surprisingly well below 1% by weight.

Water-free detergent mixtures

The present invention also relates to water-free detergent mixtures obtainable by reacting secondary or tertiary amines with alkylating agents in known manner in the absence of water or organic solvents, but in the presence of fatty alcohol polyglycol ethers with an HLB value of 6 to 12.

The detergent mixtures according to the invention are stable, i.e. neither separation nor any precipitation of salts occurs even in the event of prolonged storage. another advantage is that the mixtures are sufficiently stabilized against microbial contamination so that there is no need to add typical preservatives. This makes the compounds particularly interesting for cosmetic products.

The detergent mixtures have an excellent cleaning effect and good foaming power. They may be marketed as compounds and processed in situ to a formulation or may even be directly made up together with other surfactants and ingredients.

Compounds with the following composition:
- 30 to 70% by weight betaine
- 20 to 50% by weight fatty alcohol polyglycol ether and
- 0 to 10% by weight salt, which are obtainable by the process according to the invention, have a low viscosity and show excellent cleaning and foaming power, are dermatologically safe, readily biodegradable and can be made up, for example, into an excellent manual dishwashing detergent by addition of at most 15% by weight of water, based on the mixture as a whole.

Commercial Applications

The detergent mixtures obtainable by the process according to the invention are stable in storage and have low viscosities. Since they are obtained as water-free products, they occupy little space during storage and transport. They have excellent detergent properties and high dermatological compatibility. In addition, they are completely biodegradable.

Accordingly, the present invention also relates to the use of the water-free detergent mixtures according to the invention for the production of surface-active compositions, for example laundry detergents, dishwashing detergents and cleaning products and also hair-care and body-care products. The detergent mixtures may be used as such or after dilution with water and are then present in quantities of 1 to 90% by weight and preferably 10 to 75% by weight, based on the particular product.

The following Examples are intended to illustrate the invention without limiting it in any way.

EXAMPLES

Example 1

$C_{12/14}$ cocofatty acid amidopropyl-N,N-dimethyl aminobetaine/$C_{12/14}$ cocofatty alcohol-8 EO (HLB value: 11)

368 kg (665 moles) of an adduct of, on average, 8 moles of ethylene oxide with a technical $C_{12/14}$ cocofatty alcohol (Dehydol® LS8, a product of Henkel KGaA, Düsseldorf, FRG) were introduced into a steam-heated 1 m³ stirred tank reactor and heated to 85° C., after which 158 kg (1350 moles) of sodium chloroacetate were introduced with stirring. 409 kg (1196 moles) of hydrogenated $C_{12/14}$ cocofatty acid amidopropyl-N,N-dimethylamine were added over a period of 1 h and the mixture was kept at 90° C., the pH being adjusted to a value of 7 to 8.5. After the addition, the mixture was left to react for 5 hours until the amine value had reached 7 and showed no further reduction.

Composition of the resulting paste:
- 59% by weight betaine
- 39% by weight fatty alcohol polyglycol ether
- 2% by weight salt

Example 2

$C_{12/14}$ cocofatty acid amidopropyl-N,N-dimethyl aminobetaine/ $C_{12/14}$ cocofatty alcohol-3 EO (HLB value: 8)

309 kg (928 moles) of an adduct of, on average, 3 moles of ethylene oxide with a technical $C_{12/14}$ cocofatty alcohol (Dehydol® LS3, Henkel KGaA, Düsseldorf, FRG) were introduced into a steam-heated 1 m³ stirred tank reactor and heated to 85° C., after which 108 kg (923 moles) of sodium chloroacetate were added with stirring. 280 kg (819 moles) of hydrogenated $C_{12/14}$ cocofatty acid amidopropyl-N,N-dimethylamine were added over a period of 1 h and the mixture was kept at 90° C., the pH being adjusted to a value of 7 to 8.5. After the addition, the mixture was left to react for another 6 h until the amine value had reached 6.2 and showed no further reduction.

Composition of the resulting paste:
- 54% by weight betaine
- 44% by weight fatty alcohol polyglycol ether
- 2% by weight salt

Example 3

$C_{12/14}$ cocofatty acid amidopropyl-N,N-dimethyl aminobetaine/$C_{12/14}$ cocofatty alcohol-8 EO (HLB value: 11)

523 kg (946 moles) of an adduct of, on average, 8 moles of ethylene oxide with a technical $C_{12/14}$ cocofatty alcohol (Dehydol® LS3, a product of Henkel KGaA, Düsseldorf, FRG) were introduced into a steam-heated 1 m³ stirred tank reactor and heated to 85° C., after which 409 kg (1196 moles) of hydrogenated $C_{12/14}$ cocofatty acid amidopropyl-N,N-dimethylamine were introduced with stirring. 143 kg (1222 moles) of sodium chloroacetate were added over a period of 20 minutes and the mixture was kept at 90° C., the pH being adjusted to a value of 7 to 8.5. After the addition, the mixture was left to react for 3 hours until the amine value had reached 6.3 and showed no further reduction.

Composition of the resulting paste:
- 51% by weight betaine
- 47% by weight fatty alcohol polyglycol ether
- 2% by weight salt

Example 4

$C_{12/14}$ cocofatty acid amidopropyl-N,N-dimethyl aminobetaine/$C_8$ cocofatty alcohol-1.5 PO,6 EO (HLB value: 10.5)

448 kg (950 moles) of an adduct of, on average, 1.5 moles of propylene oxide and 6 moles of ethylene oxide with octanol were introduced into a steam-heated 1 m³ stirred tank reactor and heated to 85° C., after which 409 kg (1196 moles) of hydrogenated $C_{12/14}$ cocofatty acid amidopropyl-N,N-dimethylamine were introduced with stirring. 143 kg (1222 moles) of sodium chloroacetate were added over a period of 20 minutes and the mixture was kept at 90° C., the pH being adjusted to a value of 7 to 8.5. After the addition, the mixture was left to react for another 3 h until the amine value had reached 6.1 and showed no further reduction.

Composition of the resulting paste:
- 52% by weight betaine
- 46% by weight fatty alcohol polyglycol ether
- 2% by weight salt

What is claimed is:
1. A process for the production of a water-free detergent mixture comprising reacting at least one secondary or tertiary amine selected from the group consisting of

(i) a compound of the formula (I):

wherein $R^1$ is an alkyl or alkenyl radical having from about 6 to about 22 carbon atoms, $R^2$ is hydrogen or an alkyl radical having from 1 to about 4 carbon atoms and $R^3$ is an alkyl radical having from 1 to about 4 carbon atoms, (ii) a compound of the formula (II):

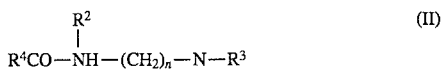

wherein $R^4CO$ is an aliphatic acyl radical having from about 6 to about 22 carbon atoms and 0 or 1 to 3 double bonds, n is 0 or a number of 1 to 3 and $R^2$ and $R^3$ are as defined above, and (iii) a compound of the formula (III):

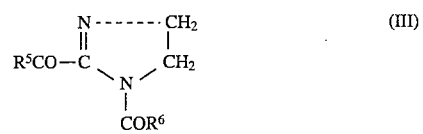

wherein each of $R^5CO$ and $R^6CO$ is independently an aliphatic acyl radical having from about 6 to about 22 carbon atoms and 0 or 1 to 3 double bonds with an alkylating agent which is a halocarboxylic acid or an alkali metal salt or ester thereof in the presence of at least one fatty alcohol polyglycol ether having an HLB value of from about 6 to about 12 and having the formula (IV):

wherein $R^7$ is an alkyl radical having from about 8 to about 14 carbon atoms, $R^8$ is hydrogen or a methyl group and n is a number of 1 to 10:
wherein the reaction is carried out in the absence of water or any additional organic solvents.

2. The process of claim 1 wherein said fatty alcohol polyglycol ether has an HLB value of 8 to 11.

3. The process of claim 1 wherein the amine to fatty alcohol polyglycol ether mole ratio is from about 2:1 to about 1:2.

4. The process of claim 1 wherein the amine to halocarboxylic acid or salt thereof mole ratio is from about 1:1.0 to about 1:1.2.

5. The process of claim 1 wherein the reaction is carried out at temperatures of from about 70° to 98° C.

6. The process of claim 1 wherein the reaction is carried out over a period of from about 1 to about 10 h.

7. The process of claim 1 wherein the reaction is carried out at a pH value of from about 6 to about 10.

8. The process of claim 1 wherein the reaction is carried out at a temperature of from about 70 to about 98° C. for a period of from about 1 to about 10 hours, and wherein the amine to fatty alcohol polyglycol ether mole ratio is from about 2:1 to about 1:2, and the amine to alkylating agent mole ratio is from about 1:1.0 to about 1:1.2.

9. The process of claim 3 wherein said mole ratio is from about 1.8:1 to about 1:1.2.

10. The process of claim 4 wherein said mole ratio is from about 1:1 to about 1:1.15.

11. The process of claim 7 wherein said pH value is from about 7 to about 8.5.

12. The process of claim 1 wherein the at least one secondary or tertiary amine is at least one tertiary amine.

13. The process of claim 1 wherein the at least one secondary or tertiary amine is $C_{12/14}$ cocofatty acid N,N-dimethyl aminopropylamide.

14. The process of claim 1 wherein the at least one secondary or tertiary amine is at least one of hexyl methylamine, hexyl dimethylamine, octyl dimethylamine, decyl dimethylamine, dodecyl methylamine, dodecyl dimethylamine, dodecyl ethyl methylamine, $C_{12/14}$ cocoalkyl dimethylamine, myristyl dimethylamine, cetyl dimethylamine, stearyl dimethylamine, stearyl ethyl methylamine, oleyl dimethylamine, $C_{16/18}$ tallow alkyl dimethylamine, and technical mixtures of the foregoing.

15. The process of claim 1 wherein the at least one fatty alcohol polyglycol ether is an adduct of 0 to 2 moles of propylene oxide and 3 to 8 moles of ethylene oxide with octanol or $C_{12/14}$ cocofatty alcohol.

16. The process of claim 1 wherein said alkylating agent is sodium chloroacetate.

* * * * *